United States Patent [19]
Redmore

[11] 3,954,761
[45] May 4, 1976

[54] PIPERAZINE PHOSPHONIC ACIDS

[75] Inventor: Derek Redmore, Ballwin, Mo.
[73] Assignee: Petrolite Corporation, St. Louis, Mo.

[22] Filed: Aug. 26, 1971
[21] Appl. No.: 175,315

Related U.S. Application Data

[62] Division of Ser. No. 768,509, Oct. 17, 1968, Pat. No. 3,674,804.

[52] U.S. Cl. .............................. 260/268 K; 210/54; 252/175; 260/47 R; 260/243 B; 260/244 R; 260/247.5 J; 260/256.4 E; 252/8.55 D
[51] Int. Cl.² ....................................... C07D 295/12
[58] Field of Search ................................ 260/268 K

[56] References Cited
UNITED STATES PATENTS
3,359,266 12/1967 Maier ................................ 260/246

*Primary Examiner*—R. J. Gallagher
*Assistant Examiner*—Jose Tovar
*Attorney, Agent, or Firm*—Sidney B. Ring; Hyman F. Glass

[57] ABSTRACT

Nitrogen-heterocyclic phosphonic acids and derivatives thereof characterized by aminomethyl (or substituted methyl) phosphonic acids or derivatives thereof bonded directly or indirectly, i.e., through a N-side chain to the nitrogen atom in the heterocyclic ring, for example those containing in the molecule at least one of the following units:

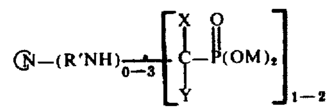

where Ⓝ represents a heterocyclic ring having a nitrogen atom on the ring; —R'N— represents an amino-terminated side chain attached directly to the ring nitrogen (which side chain may or may not be present); and

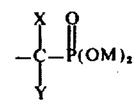

represents a methyl (or substituted methyl) phosphonic acid group where M is hydrogen, an alcohol or a salt moiety, and X and Y are hydrogen or a substituted group such as alkyl, aryl, etc., of which one or two units may be present depending on the available nitrogen bonded hydrogens, and to uses for these compounds, for example, as scale inhibitors, corrosion inhibitors, etc.

6 Claims, No Drawings

PIPERAZINE PHOSPHONIC ACIDS

Division of Ser. No. 768,509, filed Oct. 17, 1968, now U.S. Pat. No. 3,674,804, granted on July 4, 1972.

This invention relates to nitrogen-heterocyclic phosphonic acids and derivatives thereof characterized by aminomethyl (or substituted methyl) phosphonic acids or derivatives thereof bonded directly or indirectly, i.e., through an N-side chain to the nitrogen atom on the heterocyclic ring, for example those containing in the molecule at least one of the following units:

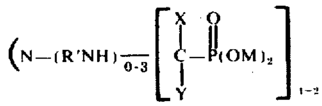

where (N represents a heterocyclic ring having a nitrogen atom in the ring, —R'N— represents an amino terminated side chain attached directly to the ring nitrogen (which side chain may or may not be present), and

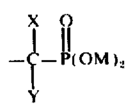

is a methyl (or substituted methyl) phosphonic acid group where M is hydrogen, an alcohol or a salt moiety, X and Y are hydrogen or a substituted group such as alkyl, aryl, etc., of which one or two units may be present depending on the available nitrogen bonded hydrogens; and to uses for these compounds, for example, as scale inhibitors, corrosion inhibitors, etc.

Any heterocyclic nitrogen compound having a reactive hydrogen group attached directly or indirectly, i.e. through an N-side chain to the ring nitrogen, which is capable of reacting with a carbonyl compound and the phosphonic acid or equivalent to yield the products of this invention may be employed. Representative examples of heterocyclic nitrogen type systems are as follows:

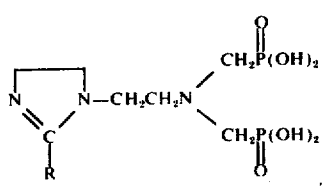

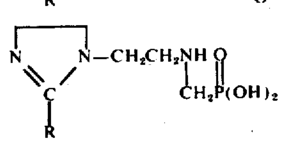

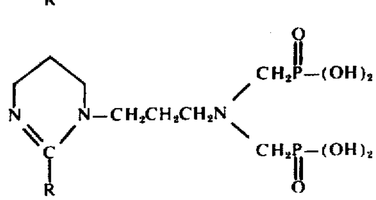

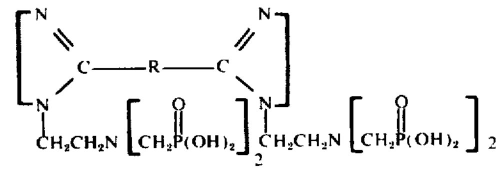

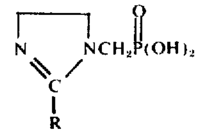

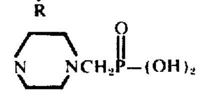

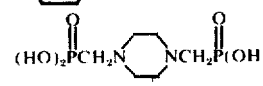

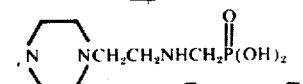

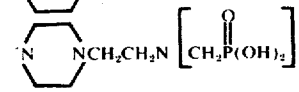

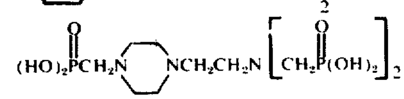

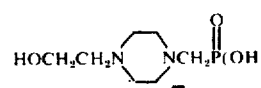

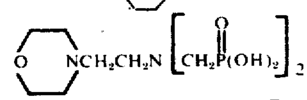

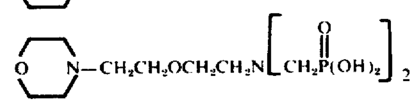

Any of the above formulae where the ring is

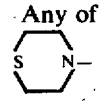

The cyclic aminomethyl phosphonic acids of this invention and their salts may be prepared by various methods. One method comprises reacting (1) a cyclic amine having reactive hydrogens attached to a nitrogen atom (2) a carbonyl compound such as an aldehyde or a ketone and (3) phosphorous acid, usually in the form of the dialkyl phosphite. The free aminomethyl phosphonic acids and their salts may be prepared by hydrolysis of the phosphonic ester under acid conditions such as with strong mineral acid such as HCl and the like.

These may be illustrated by the following reaction:

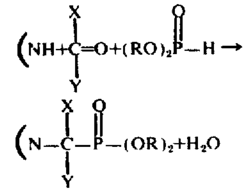

Where the cyclic amine has two N-H groups, the reaction may be

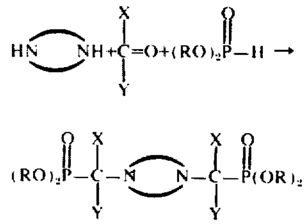

The above equation illustrates a cyclic amine wherein the NH groups are part of the ring structure itself. Also included within the scope of this invention are cyclic compounds where the reactive nitrogen group is on a N-substituted side chain, for example,

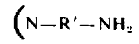

in which case corresponding reactions take place with the $NH_2$ group of the side chain, for example,

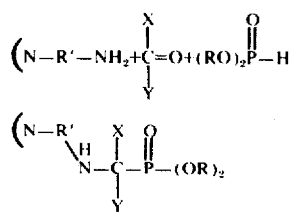

and/or

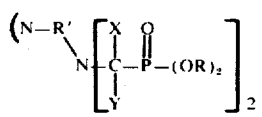

In the above equation X and Y are hydrogen or a substituted group such as an alkyl or aryl group, etc., R is an alkyl, aryl, etc. group, and R' is a substituted group, for example alkylene, arylene, oxyalkylene, polyoxyalkylene, polyalkylene amino, etc.

Phosphonic esters are converted to phosphonic acids or salts thereof according to the following reaction

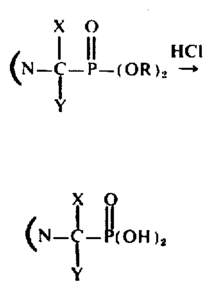

and/or

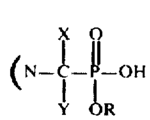

and other corresponding reactions.

Salts of these can also be prepared, for example salts containing metal, ammonium, amine, etc. groups such as sodium, potassium, triethanolamine, diethanolamine.

A second method comprises reacting (1) a cyclic amine (2) a carbonyl compound such as aldehyde or a ketone and (3) phosphorous acid preferably in presence of a strong mineral acid such as hydrochloric acid. This method yields the aminomethyl phosphonic acids directly.

These may be illustrated by the following reactions:

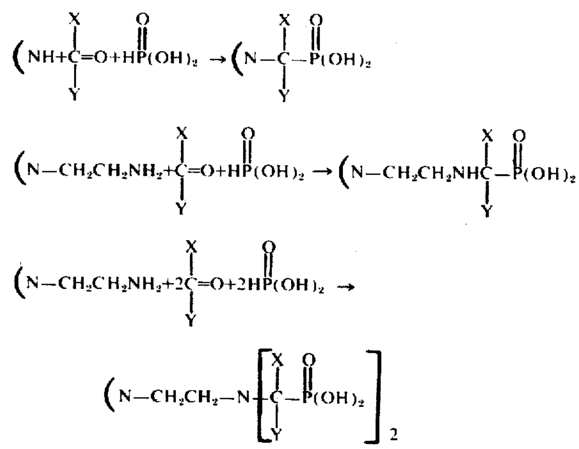

The following examples are presented for purpose of illustration and not of limitation.

EXAMPLES

EXAMPLE 1

To a stirred mixture of 2-heptyl-2-imidazoline (45.5g; 0.25 mole) and diethyl phosphite (34.5g; 0.25 mole) was added a 40% aqueous formaldehyde solution (19 mls; 0.25 mole) during 15 minutes. The reaction was rapid and exothermic giving a reaction temperature of 80°. The mixture was stirred for 1 hour following the addition. Hydrolysis of the resulting phosphonate ester was carried out by heating the ester with 18% hydrochloric acid (200 ml) for 6 hours. Evaporation of the aqueous acid under vacuum yielded the phosphonic acid whose structure is represented below

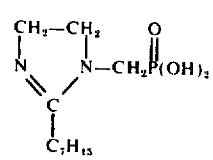

EXAMPLE 2

2-heptyl-2-imidazoline (62g; 0.33 mole) was dissolved in a mixture of hydrochloric acid (100 ml), phosphorous acid (28g; 0.33 mole) and water (100 ml). This solution was heated and stirred under gentle reflux while 40% aqueous formaldehyde solution (25 mls; 0.33 mole) was added during 45 minutes. Heating was continued for 1 hour and the volatiles were removed under vacuum. The residue was the imidazoline phosphonic identical with that of Example 1.

EXAMPLE 3

1-(2′-aminoethyl)-2-heptadecyl-2-imidazoline (88.8g; 0.25 mole) was heated under reflux with phosphorous acid (21g; 0.25 mole) and hydrochloric acid (50 ml) in water (100 ml). To this stirred mixture was added 40% aqueous formaldehyde (20 ml; 0.25 mole) during 1 hour. Heating was continued for a further 1 hour before the aqueous acid was removed under vacuum. The resulting water soluble phosphonic acid is represented by the following structure:

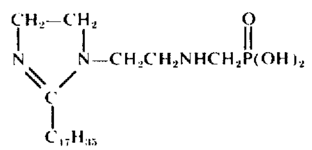

EXAMPLE 4

Using the procedure of Example 3, the same imidazoline (0.25 mole) was reacted with phosphorous acid (0.5 mole) and formaldehyde (0.5 mole) in the presence of hydrochloric acid (100 ml) and water (100 ml). The product can be represented by the following formula:

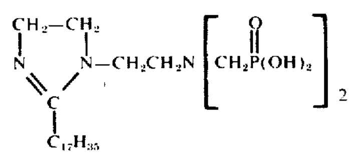

EXAMPLE 5

N-(2-aminoethyl) piperazine (32.3g; 0.25 mole) was stirred and heated under reflux with phosphorous acid (20.5g; 0.25 mole) and hydrochloric acid (50 ml) in water (50 ml). During 30 mins. a 40% aqueous solution of formaldehyde (20 ml; 0.25 mole) was added to above solution. After heating for an additional period of 1½ hours, the aqueous acids were removed under vacuum to yield an aminomethyl phosphonic acid. The product consists mainly of the acid represented by the following formula:

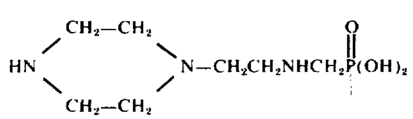

EXAMPLE 6

Using the procedure of Example 5, N-(2-aminoethyl) piperazine (0.25 mole) was reacted with phosphorous acid (0.5 mole) and formaldehyde (0.5 mole) in presence of hydrochloric acid. The product consists of a mixture of acids whose main components are represented by the following formulae:

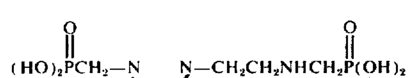

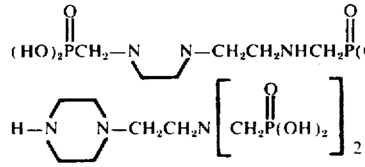

EXAMPLE 7

Following the procedure of Example 6 N-(aminoethyl) piperazine (0.25 mole) was reacted with phosphorous acid (0.75 mole) and formaldehyde (0.75 mole) in presence of hydrochloric acid. The product is a triphosphonic acid represented by the formula:

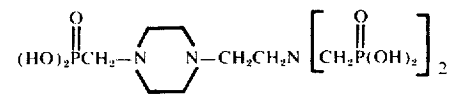

EXAMPLE 8

N-(2-aminoethyl) morpholine (32.5; 0.25 mole) was heated and stirred under reflux with phosphorous acid (20.5g; 0.25 mole) and hydrochloric acid (50 ml) in water (50 ml). To this solution 40% aqueous formaldehyde (20 ml; 0.25 mole) was added during 45 minutes. Heating was continued for 1 hour before aqueous acid was removed under vacuum. The resulting product was the methyl phosphonic acid represented below:

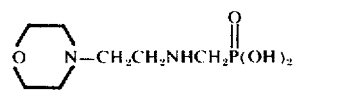

EXAMPLE 9

N-(2-aminoethyl) morpholine (32.5g; 0.25 mole) was heated and stirred under reflux with phosphorous acid (20.5g; 0.25 mole) and hydrochloric acid (60 ml) in water (60 ml). To this solution was added acetone (15g; 0.25 mole) during 1 hour and the heating was continued for a further 3 hours. Evaporation of the solvent under vacuum yielded the crude phosphonic acid represented by the following formula:

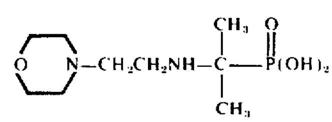

EXAMPLE 10

This example illustrates the use of crude amine mixtures in the preparation of aminomethyl phosphonic acids. Amine AL-1 (Jefferson Chemical Co.) (60g.), [which consists of a mixture of N-(2-aminoethyl) piperazine (40%), N-(2-hydroxyethyl) piperazine (10–15%) and higher amines] was reacted in the manner of previous examples with phosphorous acid (82g; 1 mole) and 40% formaldehyde (75 ml; 1 mole) in presence of hydrochloric acid (200 ml) and water (200 ml). Evaporation of the solvents in vacuum yielded a phosphonic acid mixture containing as major components the following acids:

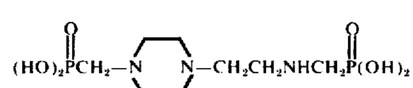

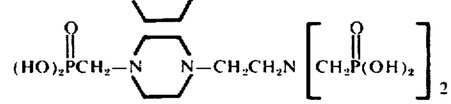

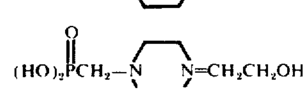

CYCLIC AMIDINES

The expression "cyclic amidine" is employed in its usual sense to indicate ring compounds in which there are present either 5 or 6 members, and having 2 nitrogen atoms separated by a single carbon atom supplemented by either two additional carbon atoms or three additional carbon atoms in the main chain completing the ring. All the carbon atoms may be substituted. The nitrogen atom of the ring, involving monovalent linkages (the 1-position) may be unsubstituted or substituted for example, an alkylene amine group, a polyalkylene amino group, etc.

These cyclic amidines are further characterized as being substituted imidazolines and tetrahydropyrimidines in which the two-position carbon of the ring is generally bonded to a hydrocarbon radical or comparable radical derived from an acid, such as a low molal fatty acid, a high molal fatty acid, or comparable acids, aromatic acids, polycarboxy acids, acids containing heterocyclic rings, and the like.

For details of the preparation of imidazolines from amines, see the following U.S. Pat. Nos., U.S. Pat. No. 1,999,989 dated Apr. 30, 1935, Max Bockmuhl et al.; U.S. Pat. No. 2,155,877 dated Apr. 25, 1939, Edmund Waldmann et al.; and U.S. Pat. No. 2,155,878 dated Apr. 25, 1939, Edmund Waldman et al. Also see Chem. Rev. 32, 47 (43), Chem. Rev. 54, 593 (54), and "Imidazole and Derivatives, I" by K. Hofmann (1953).

Equally suitable for use in preparing compounds useful in this invention and for the preparation of tetrahydropyrimidines substituted in the 2-position are the corresponding polyamines containing at least one primary amino group separated from the first primary amino group by three carbon atoms instead of being separated by only 2 carbons as with imidazolines. This reaction, as in the case of the imidazolines, is generally carried out by heating the reactants to a temperature at which 2 moles of water are evolved and ring closure is effected. For details of the preparation of tetrahydropyrimidines, see German Pat. No. 700,371 dated Dec. 18, 1940, to Edmund Waldmann and August Chwala; German Pat. No. 701,322 dated Jan. 14, 1941, to Karl Kiescher, Ernst Urech and Willi Klarer, and U.S. Pat. No. 2,194,419 dated Mar. 19, 1940, to August Chwala.

Substituted imidazolines and tetrahydropyrimidines are obtained from a variety of acids beginning with the one carbon acid (formic) through and including higher fatty acids or the equivalent having 1–30 or more carbon atoms such as from 8–22 carbons. Modified fatty acids also can be employed as, for example, phenyl stearic acid or the like. Cyclic acids may be employed, including naphthenic acids. A variety of other acids, including benzoic acid, etc., from which the C of the residue

is part of the ring. The fatty acids employed, for example, may be saturated or unsaturated. Branched long chain fatty acids may be employed. See J. Am. Chem. Soc. 74, 2523 (1952). This applies also to the lower molecular weight acids as well.

The nitrogen phosphonic acids more specifically are of the formula

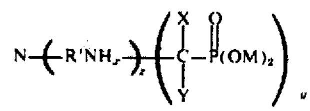

where $x$ is 0 or 1, $y$ is 1 or 2 and $z$ is 0 or 1 with the provisos that (1) $y$ is 1 when $z$ is 0 and (2) $x$ is 1 and $y$ is 1 when $z$ is 1 and (3) $x$ is 0 when $y$ is 2 and $z$ is 1.

As is well known, cyclic amidines containing the 1-position a substituted group can be prepared by reacting a suitable amine with the desired carboxylic acid under suitable conditions so as to remove 2 moles of water for each equivalent of carboxylate radical. Thus, where one employs a diamine such as ethylene or propylene diamine, a cyclic amidine which is unsubstituted in the 1-position is obtained.

Alternatively amino and polyamino substituted cyclic amidine compounds can be prepared from polyamines such as a triamine or higher amines, for example, diethylene triamine, triethylene tetramine, tetraethylene pentamine, corresponding propylene analogues, etc. Thus, when one reacts diethylene triamine with a carboxylic acid or its esters, one obtains

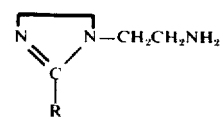

and with triethylene tetramine one obtains

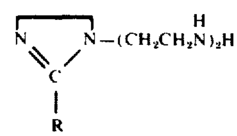

It should be noted that Z can also be part of an aromatic ring. Thus, by reacting

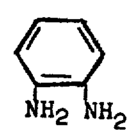

with a carboxylic acid one obtains

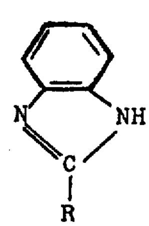

Thus, cyclic amidines within the scope of this invention comprise compounds of the formulae:

(1)

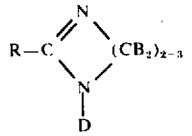

(2)

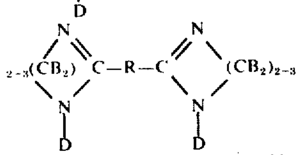

(3)

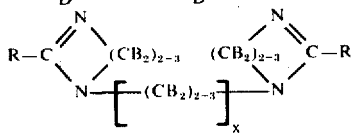

where RC= and =C—R—C= are the residues derived from the carboxylic acid, monocarboxylic acids in (1) and (3), and dicarboxylic acids in (2), where R comprises a hydrocarbon radical having, for example, 1–30 carbon atoms, hydrocarbons in which the carbon atom chain is interrupted by oxygen, etc.; and B is a hydrogen or a hydrocarbon radical; D is hydrogen or a radical, for example $—(AX)_nH$ where X is amino, A is an alkylene radical containing, for example, 2–3 carbons in its main chain wherein $n$ and $x$ are numbers, for example, 1–10 or higher, advantageously 1–3, but preferably 1, and $(CB_2)_n$ is, for example, a divalent radical of the formula:

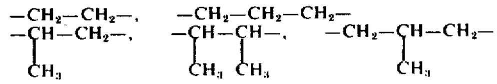

In (2) $CB_2$'s and the 1-substituted side chain may be the same or different.

Actually, substituted cyclic amidines can be obtained from a variety of polyamines. From a practical standpoint, however, the most readily available polyamines are ethylene diamine, diethylene triamine, triethylene tetramine, and tetraethylene pentamine. However, other polyamines having some other divalent radical, such as

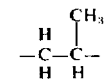

can be employed.

The following Table is limited to derivatives of the four most readily available polyamines above indicated.

TABLE 1

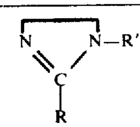

| Ex. No. | RCOOH source of RC= | R' |
|---|---|---|
| 1a | Lauric | $CH_2CH_2NH_2$ |
| 2a | Hexanoic | $CH_2CH_2NH_2$ |
| 3a | Isovaleric | $CH_2CH_2NH_2$ |
| 4a | Stearic | $Ch_2CH_2NH_2$ |
| 5a | Melissic | $CH_2CH_2NH_2$ |
| 6a | Phenyl stearic | $CH_2CH_2NH_2$ |
| 7a | Benzoic | $CH_2CH_2NH_2$ |
| 8a | Cresotinic | $CH_2CH_2NH_2$ |
| 9a | Naphthenic | $CH_2CH_2NH_2$ |
| 10a | Oleic | $CH_2CH_2NH_2$ |
| 11a | do | $CH_2CH_2NHCH_2CH_2NH_2$ |
| 12a | Pelargonic | $CH_2CH_2NHCH_2CH_2NH$ |
| 13a | Lauric | $CH_2CH_2NHCH_2CH_2NH$ |
| 14a | Palmitic | $CH_2CH_2NHCH_2CH_2NH$ |
| 15a | Cerotic | $CH_2CH_2NHCH_2CH_2NH$ |
| 16a | p-Tert-butyl benzoic | $CH_2CH_2NHCH_2CH_2NH$ |
| 17a | p-Methoxy benzoic | $CH_2CH_2NHCH_2CH_2NH$ |
| 18a | Toluic | $CH_2CH_2NHCH_2CH_2NH$ |
| 19a | Naphthenic | $CH_2CH_2NH_2CH_2CH_2NH_2$ |
| 20a | p-Hydroxy benzoic | $CH_2CH_2NH_2CH_2CH_2NH_2$ |
| 21a | Formic | $CH_2CH_2NHCH_2CH_2NHCH_2CH_2NH_2$ |
| 22a | Methyloctadecanoic | $CH_2CH_2NHCH_2CH_2NHCH_2CH_2NH_2$ |
| 23a | Capric | $CH_2CH_2NHCH_2CH_2NHCH_2CH_2NH_2$ |
| 24a | Stearic | $CH_2CH_2NHCH_2CH_2NHCH_2CH_2NH_2$ |
| 25a | Phenylstearic | $CH_2CH_2NHCH_2CH_2NHCH_2CH_2NH_2$ |
| 26a | Cresotinic | $CH_2CH_2NHCH_2CH_2NHCH_2CH_2NH_2$ |
| 27a | Linoleic | $CH_2CH_2NHCH_2CH_2NHCH_2CH_2NH_2$ |
| 28a | Oleic | $CH_2CH_2NHCH_2CH_2NHCH_2CH_2NH_2$ |
| 29a | 3-methoxybenzoic | $CH_2CH_2NHCH_2CH_2NHCH_2CH_2NH_2$ |
| 30a | Naphthenic | $CH_2CH_2NHCH_2CH_2NHCH_2CH_2NH_2$ |
| 31a | Lauric | $CH_2CH_2NHCH_2CH_2NHCH_2CH_2NH_2$ |
| 32a | Benzoic | $CH_2CH_2NHCH_2CH_2NHCH_2CH_2NH_2$ |

The only polyamines available on a large scale for the manufacture of tetrahydropyrimidines are propylene diamine and 3,3'-iminobispropylamine. This latter product can be converted into the tetramine or pentamine by appropriate reaction with a suitable imine or by reaction with acrylonitrile, followed by the usual steps of converting the intermediate into the amine. Tetrahydropyrimidines, comparable to the imidazolines of Table I appear in Table II, immediately following.

TABLE II

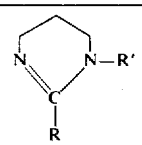

| Ex. No. | RCOOH source of RC | R' |
|---|---|---|
| 1b | Formic | $CH_2CH_2CH_2NH_2$ |
| 2b | Acetic | $CH_2CH_2CH_2NH_2$ |
| 3b | Butyric | $CH_2CH_2CH_2NH_2$ |
| 4b | Valeric | $CH_2CH_2CH_2NH_2$ |
| 5b | Isovaleric | $CH_2CH_2CH_2NH_2$ |
| 6b | Phenyl acetic | $CH_2CH_2CH_2NH_2$ |
| 7b | Pelargonic | $CH_2CH_2CH_2NH_2$ |
| 8b | Lauric | $CH_2CH_2CH_2NH_2$ |
| 9b | Stearic | $CH_2CH_2CH_2NH_2$ |
| 10b | Arachidic | $CH_2CH_2CH_2NH_2$ |
| 11b | Eicosane-carboxylic | $CH_2CH_2CH_2NH_2$ |

TABLE II-continued

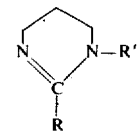

| Ex. No. | RCOOH source of RC | R' |
|---|---|---|
| 12b | Cerotic | $CH_2CH_2CH_2NH_2$ |
| 13b | Melissic | $CH_2CH_2CH_2NH_2$ |
| 14b | Phenyl stearic | $CH_2CH_2CH_2NH_2$ |
| 15b | Benzoic | $CH_2CH_2CH_2NH_2$ |
| 16b | p-Methoxy benzoic | $CH_2CH_2CH_2NH_2$ |
| 17b | Cresotinic | $CH_2CH_2CH_2NH_2$ |
| 18b | Salicylic | $CH_2CH_2CH_2NH_2$ |
| 19b | p-tert-Butylbenzoic | $CH_2CH_2CH_2NH_2$ |
| 20b | p-Ethoxy benzoic | $CH_2CH_2CH_2NH_2$ |
| 21b | Oleic | $CH_2CH_2CH_2NH_2$ |
| 22b | Undecylenic | $CH_2CH_2CH_2NH_2$ |
| 23b | Linoleic | $CH_2CH_2CH_2NH_2$ |
| 24b | Hydroxy butyric | $CH_2CH_2CH_2NH_2$ |
| 25b | Methloctadecanoic | $CH_2CH_2CH_2NH_2$ |
| 26b | Naphthenic | $CH_2CH_2CH_2NH_2$ |
| 27b | Palmitic | $CH_2CH_2CH_2NH_2$ |

The procedure employed in the manufacture of suitable substituted imidazolines from dicarboxylic acids is comparable to that employed when monocarboxylic acids are used as reactants. Suitable amines derived from the three amines previously noted are described in Table III.

TABLE III

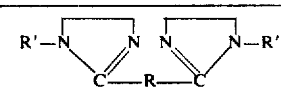

| Ex. No. | HOOC—R—COOH source of —CRC— | R' |
|---|---|---|
| 1c | Succinic | $CH_2CH_2NH_2$ |
| 2c | Adipic | $CH_2CH_2NH_2$ |
| 3c | Suberic | $CH_2CH_2NH_2$ |
| 4c | Sebacic | $CH_2CH_2NH_2$ |
| 5c | Nonodecane dicarboxylic | $CH_2CH_2NH_2$ |
| 6c | Diglycolic | $CH_2CH_2NH_2$ |
| 7c | Ethylene bis(glycolic) | $CH_2CH_2NH_2$ |
| 8c | Methylene dibenzoic | $CH_2CH_2NH_2$ |
| 9c | Stearyl malonic | $CH_2CH_2NH_2$ |
| 10c | Phthalic | $CH_2CH_2NH_2$ |
| 11c | Succinic | $CH_2CH_2NHCH_2CH_2NH_2$ |
| 12c | Glutaric | $CH_2CH_2NHCH_2CH_2NH_2$ |
| 13c | Pimelic | $CH_2CH_2NHCH_2CH_2NH_2$ |
| 14c | Azelaic | $CH_2CH_2NHCH_2CH_2NH_2$ |
| 15c | Eiocasane dicarboxylic | $CH_2CH_2NHCH_2CH_2NH_2$ |
| 16c | Dilinoleic | $CH_2CH_2NHCH_2CH_2 NH_2$ |
| 17c | Isophthalic | $CH_2CH_2NHCH_2CH_2NH_2$ |
| 18c | Diglycolic | $CH_2CH_2NHCH_2CH_2NH_2$ |
| 19c | Lauryl malonic | $CH_2CH_2NHCH_2CH_2NH_2$ |
| 20c | Methylene dibenzoic | $CH_2CH_2NHCH_2CH_2NH_2$ |
| 21c | Adipic | $CH_2CH_2NHCH_2CH_2NHCH_2CH_2NH_2$ |
| 22c | Succinic | $CH_2CH_2NHCH_2CH_2NHCH_2CH_2NH_2$ |
| 23c | Suberic | $CH_2CH_2NHCH_2CH_2NHCH_2CH_2NH_2$ |
| 24c | Pimelic | $CH_2CH_2NHCH_2CH_2NHCH_2CH_2NH_2$ |
| 25c | Nonedecane dicarboxylic | $CH_2CH_2NHCH_2CH_2NHCH_2CH_2NH_2$ |
| 26c | Dlglycolic | $CH_2CH_2NHCH_2CH_2NHCH_2CH_2NH_2$ |
| 27c | Methylene dibenzoic | $CH_2CH_2NHCH_2CH_2NHCH_2CH_2NH_2$ |
| 28c | Stearyl malonic | $CH_2CH_2NHCH_2CH_2NHCH_2CH_2NH_2$ |
| 29c | Stearyl succinic | $CH_2CH_2NHCH_2CH_2NHCH_2CH_2NH_2$ |
| 30c | Terephthalic | $CH_2CH_2NHCH_2CH_2NHCH_2CH_2NH_2$ |
| 31c | Dilinoleic | $CH_2CH_2NHCH_2CH_2NHCH_2CH_2NH_2$ |
| 32c | Phthalic | $CH_2CH_2NHCH_2CH_2NHCH_2CH_2NH_2$ |

In the use of dicarboxy acid, the bulk of the examples were obtained from 3,3'-iminobispropylamine. These compounds which appear in Table IV are comparable to those which appeared in Table III preceding.

TABLE IV

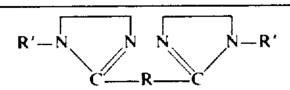

| Ex. No. | HOOC—R—COOH source of —CRC— | R' |
|---|---|---|
| 1d | Alkenylsuccinic (alkenyl $C_{12}$) | $CH_2CH_2CH_2NH_2$ |
| 2d | Succinic | $CH_2CH_2CH_2NH_2$ |
| 3d | Glutaric | $CH_2CH_2CH_2NH_2$ |
| 4d | Adipic | $CH_2CH_2CH_2NH_2$ |
| 5d | Suberic | $CH_2CH_2CH_2NH_2$ |
| 6d | Sebacic | $CH_2CH_2CH_2NH_2$ |
| 7d | Pimelic | $CH_2CH_2CH_2NH_2$ |
| 8d | Azelaic | $CH_2CH_2CH_2NH_2$ |
| 9d | Nonodecane dicarboxylic | $CH_2CH_2CH_2NH_2$ |
| 10d | Eicosane dicarboxylic | $CH_2CH_2CH_2NH_2$ |
| 11d | Diglycolic | $CH_2CH_2CH_2NH_2$ |
| 12d | Ethylene bisglycolic | $CH_2CH_2CH_2NH_2$ |
| 13d | Methylene disalicyclic | $CH_2CH_2CH_2NH_2$ |
| 14d | Dilinoleic | $CH_2CH_2CH_2NH_2$ |
| 15d | Stearyl malonic | $CH_2CH_2\ CH_2NH_2$ |
| 16d | Lauryl succinic | $CH_2CH_2CH_2NH_2$ |
| 17d | Isotetradecyl succinic | $CH_2CH_2CH_2NH_2$ |
| 18d | Phthalic | $CH_2CH_2CH_2NH_2$ |
| 19d | Isophthalic | $CH_2CH_2CH_2NH_2$ |
| 20d | Terephthalic | $CH_2CH_2CH_2NH_2$ |
| 21d | Phenyl acetic | $CH_2CH_2CH_2NH_2$ |
| 22d | Maleic | $CH_2CH_2CH_2NH_2$ |

In addition, cyclic amidines of the following type can also be employed:

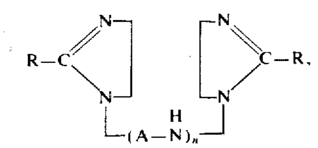

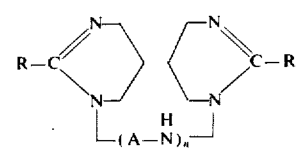

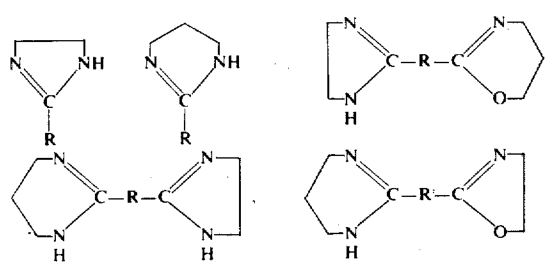

In addition, the cyclic amidine structure may be substituted with other than a hydrocarbon group, for example, a sulfur containing group such as

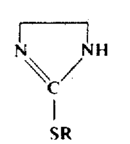

wherein R is a substituted group for example, a hydrocarbon group alkyl, aryl, etc.

Imidazolidines, thiazolidines, diazolidines and their six-membered ring analogues can also be employed, for example

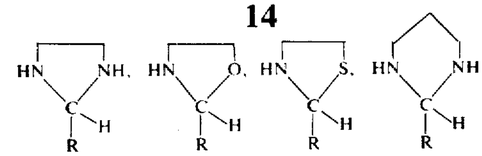

etc.

In addition, other N-heterocyclic systems can be employed, for example, those in which nitrogen is the only heterocyclic atom in the ring, where N is present with other heterocyclic atoms such as oxygen, sulfur, etc., where more than one nitrogen and/or more than one other heterocyclic atom is present, where the heterocyclic system containing one ring or more than one ring, where the ring nitrogen is reacted or where the side chain nitrogen or both are reacted, etc.

Thus (N indicates compounds having one or more rings with one or more nitrogen atoms in the ring which rings may contain one or more nitrogen atom in at least one or more of the rights but not necessarily in all the rings, i.e. some of the rings may contain only carbon and hydrogen and/or other heterocyclic atoms.

As is quite evident, other heterocyclic amines, carbonyls and phosphorous derivatives can be employed herein to yield products useful in this invention. It is, therefore, not only impossible to attempt a comprehensive catalogue of such compositons, but to attempt to describe the invention in its broader aspects in terms of specific chemical names of reactants would be too voluminous and unnecessary since one skilled in the art could by following the description of the invention herein select proper reagents. This invention lies in the use of suitable heterocyclic amines, carbonyl, and phosphorous derivatives which can be used to form the heterocyclic amino methyl phosphonic acids and derivatives thereof of this invention. To precisely define each specific useful reactant in light of the present disclosure would merely call for chemical knowledge within the skill of the art in a manner analogous to a mechanical engineer who prescribes in the construction of a machine the proper materials and the proper dimensions thereof. From the description in this specification and with the knowledge of a chemist, one will know or deduce with confidence the applicability of specific reactants suitable in this invention by applying them in the process set forth herein to form phosphonic acid derivatives. In analogy to the case of a machine, wherein the use of certain materials of construction or dimensions of parts would lead to no practical useful result, various materials will be rejected as inapplicable where others would be operative. One can obviously assume that no one will wish to use a useless amine or a useless phosphorous derivative nor will be misled because it is possible to misapply the teachings of the present disclosure to do so. Thus, any heterocyclic amine, carbonyl and phosphorous derivative that can react to form heterocyclic aminomethyl phosphonic acid and derivatives thereof can be employed.

USE AS SCALE INHIBITORS

This phase of the invention relates to methods of inhibiting scale formation and/or the formation of solid scale-forming salts in water or brine comprising adding to said water or brine small amounts of cyclic amino phosphonate compounds of this invention.

Most commercial water contains alkaline earth metal cations, such as calcium, barium, magnesium, etc., and several anions such as bicarbonate, carbonate, sulfate, oxalate, phosphate, silicate, fluoride, etc. When combinations of these anions and cations are present in concentrations which exceed the solubility of their reaction products, precipitates form until these product solubility concentrations are no longer exceeded. For example, when the concentrations of calcium ion and carbonate ion exceed the solubility of the calcium carbonate reaction product, a solid phase of calcium carbonate will form.

Solubility product concentrations are exceeded for various reasons, such as evaporation of the water phase, change in pH, pressure or temperature, and the introduction of additional ions which form insoluble compounds with the ions already present in the solution.

As these reaction products precipitate on the surfaces of the water carrying system, they form scale. The scale prevents effective heat transfer, interferes with fluid flow, facilitates corrosive processes, and harbors bacteria. This scale is an expensive problem in many industrial water systems, causing delays and shutdowns for cleaning and removal.

I have now discovered that the use of the cyclic aminomethyl phosphonates of this invention inhibits the formation of scale.

The cyclic aminomethyl phosphonates of this invention were also found to exhibit good deflocculating or dispersing properties and good surfactancy properties. It is highly unusual for both of these properties to be effectively exhibited by the same compound. As can be appreciated, such compounds can advantageously be utilized in applications which can use the foregoing properties, such as, detergent compositions. In many detergent applications such as textile washing and hard surface cleaning, the ability of the detergent composition to remove the soil and keep the soil suspended in the washing medium is of paramount importance.

As used in detergent compositions, the compounds of the instant invention are preferably formulated with other components, i.e. builders such as sodium tripolyphosphate, anti-redeposition agents such as carboxymethyl cellulose, brightening agents and the like, in amounts between about 10% to 50% by weight of the detergent composition.

The esters of cyclic aminomethyl phosphonic acids were found not only to be completely miscible with water but also highly soluble in organic solvents, such as hydrocarbon solvent, i.e. hexane and pentane, carbon tetrachloride, haloethylene solvents, i.e., perchloroethylene, ethers, alcohols, and the like. Also, the esters were found to impart a solubilizing action to water in water-immiscible solvents, such as many of the previously mentioned solvents. This totally unexpected property render them highly useful as gasoline de-icer additives and along with their surfactancy properties render them useful as dry cleaning detergents. As can be appreciated, however, the unique ability to impart a solubilizing action to water in water-immiscible solvents can be utilized in many and varied applications and therefore the esters of cyclic aminomethyl phosphonates are preferred in applications which use the combined surfactancy and/or water solubilizing properties.

The following examples are presented to illustrate the use of the cyclic phosphonates prescribed herein and are presented for purposes of illustration and not of limitation.

The following test was used to evaluate these compositions as scale inhibitors.

Procedure:

1. Make up stock $CaCl_2 \cdot 2H_2O$. 2.94 g/L or 56 g/5 gallons (18.9 liters)
2. Stock $NaHCO_3$ should be 3.35 g/L or 64 g/5 gallons.
3. Inhibitors — Make 0.1% solutions in deionized water. 1 ml in 100 sample = 10 ppm (Test at 5, 20, and 50 ppm.)

Put 50 ml bicarbonate solution into 100 ml milk dilution bottle. Add inhibitor (for 100 ml final volume). Then add 50 ml $CaCl_2$ solution and set in bath at 180°F. Do not cap. Always prepare a blank. Run a hardness determination on a 50—50 mixture before heating.

Heat at 180°F. Take 10 ml samples from bottles after 2 hours and 4 hours.

Filter through millipore filter.

Run total hardness on filtrate.

Calculate as % Ca still in solution, i.e., $$\frac{\text{Total hardness after heating}}{\text{Total hardness before heating}} \times 100 = \%$$

All of the compounds were tested at 180°F, at 5, 20, and 50 ppm levels. Hardness readings were taken after 2 and 4 hours.

TABLE A

SCALE INHIBITORS

| Ex. | Scale Inhibitor Composition Prepared according to | % Protection after 4 hours at the following Concentrations 20 ppm | 50 ppm |
|---|---|---|---|
| 1 | Example 2 | 24 | 48 |
| 2 | Example 3 | 25 | 43 |
| 3 | Example 5 | 33 | 35 |
| 4 | Example 6 | 33 | 44 |
| 5 | Example 8 | 33 | 34 |
| 6 | Example 10 | 32 | 76 |
| 7 | 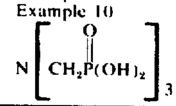 | 25 | 29 |

The above tests illustrate the superiority of the cyclic phosphonic acids over the aliphatic phosphonic acids (Ex. 7).

USE AS CORROSION INHIBITORS

This phase of this invention relates to the use of these compounds in inhibiting the corrosion of metals, most particularly iron, steel and ferrous alloys. These compounds can be used in a wide variety of applications and systems where iron, steel and ferrous alloys are affected by corrosion. They may be employed for inhibiting corrosion in processes which require a protective or passivating coating as by dissolution in the medium which comes in contact with the metal. They can be used in preventing atmospheric corrosion, underwater corrosion, corrosion in steam and hot water systems, corrosion in chemical industries, underground corrosion, etc.

The corrosion inhibitors contemplated herein find special utility in the prevention of corrosion of pipe or equipment which is on contact with a corrosive oil-containing medium, as, for example, in oil wells producing corrosive oil or oil-brine mixtures, in refineries, and the like. These inhibitors may, however, be used in other systems or applications. They appear to possess properties which impart to metals resistance to attack by a variety of corrosive agents, such as brines, weak inorganic acids, organic acids, $CO_2$, $H_2S$, air or oxygen, etc.

The method of carrying out this process in relatively simple in principle. The corrosion preventive reagent is dissolved in the liquid corrosive medium in small amounts and is thus kept in contact with the metal surface to be protected. Alternatively, the corrosion inhibitor may be applied first to the metal surface, either as is, or as a solution in some carrier liquid or paste. Continuous application, as in the corrosive solution, is the preferred method, however.

The present process finds particular utility in the protection of metal equipment of oil and gas wells, especially those containing or producing an acidic constituent such as $H_2S$, $CO_2$, air or oxygen, organic acids and the like. For the protection of such wells, the reagent, either undiluted or dissolved in a suitable solvent, is fed down the annulus of the well between the casing and producing tubing where it becomes commingled with the fluid in the well and is pumped or flowed from the well with these fluids, thus contacting the inner wall of the casing, the outer and inner wall of tubing, and the inner surface of all wellhead fittings, connections and flow lines handling the corrosive fluid.

Where the inhibitor composition is a liquid, it is conventionally fed into the well annulus by means of a motor driven chemical injector pump, or it may be dumped periodically (e.g., once every day or two) into the annulus by means of a so-called "boll weevil" device or similar arrangement. Where the inhibitor is a solid, it may be dropped into the well as a solid lump or stock, it may be blown in as a powder with gas, or it may be washed in with a small stream of the well fluids or other liquid. Where there is gas pressure on the casing, it is necessary, of course, to employ any of these treating methods through a pressure equalizing chamber equipped to allow introduction of reagent into the chamber, equalization of pressure between chamber and casing, and travel of reagent from chamber to well casing.

Occasionally, oil and gas wells are completed in such a manner that there is no opening between the annulus and the bottom of the tubing or pump. This results, for example, when the tubing is surrounded at some point by a packing held by the casing or earth formation below the casing. In such wells the reagent may be introduced into the tubing through a pressure equalizing vessel, after stopping the flow or bluids. After being so treated, the well should be left closed in for a period of time sufficient to permit the reagent to drop to the bottom of the well.

For injection into the well annulus, the corrosion inhibitor is usually employed as a solution in a suitable solvent. The selection of solvent will depend much upon the specific reagent being used and its solubility characteristics.

For treating wells with packed-off tubing, the use of solid "sticks" or plugs of inhibitor is especially convenient. These may be prepared by blending the inhibitor with a mineral wax, asphalt or resin in a proportion sufficient to give a moderately hard and high-melting solid which can be handled and fed into the well conveniently.

The protective action of the herein described reagents appears to be maintained for an appreciable time after treatment ceases, but eventually is lost unless another application is made.

For example, for the protection of gas wells and gas-condensate wells, the amount of corrosion inhibitor used might range between about ¼ to 3 lbs. per million cubic feet of gas produced, depending upon the amounts and composition of corrosive agents in the gas and the amount of liquid hydrocarbon and water produced. However, in no case does the amount of inhibitor required appear to be stoichiometrically related to the amount of acids produced by a well, since protection is obtained with much less corrosion inhibitor than usually would be required for neutralization of the acids produced.

These compounds are particularly effective in the prevention of corrosion in systems containing a corrosive aqueous medium, and most particularly in systems containing brines.

These reagents can also be used in the prevention of corrosion in the secondary recovery of petroleum by water flooding and in the disposal of waste water and brine from oil and gas wells. Still more particularly, they can be used in a process of preventing corrosion in water flooding and in the disposal of waste water and brine from oil and gas wells which is characterized by injecting into an underground formation an aqueous solution containing minor amounts of the compositions of this invention, in sufficient amounts to prevent the corrosion of metals employed in such operation.

When an oil well ceases to flow by the natural pressure in the formation and/or substantial quantities of oil can no longer be obtained by the usual pumping methods, various processes are sometimes used for the treatment of the oil-bearing formation in order to increase the flow of oil. These processes are usually described as secondary recovery processes. One such process which is used quite frequently is the water flooding process wherein water is pumped under pressure into what is called an "injection well" and oil, along with quantities of water, that have been displaced from formation, are pumped out of an adjacent well usually referred to as a "producing well". The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system". If the water is recirculated in a closed system without substantial aeration, the secondary recovery method is referred to herein as a "closed water flooding system".

Because of the corrosive nature of oil field brines, to economically produce oil by water flooding, it is necessary to prevent or reduce corrosion since corrosion increases the cost thereof by making it necessary to repair and replace such equipment at frequent intervals.

I have discovered a method of preventing corrosion in systems containing a corrosive aqueous media, and most particularly in systems containing brines, which is characterized by employing the compounds described herein. For example, I have discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation an aqueous solution of the compositions of this invention.

The invention, then, is particularly concerned with preventing corrosion in a water flooding process characterized by the flooding medium, containing an aqueous or an oil field brine solution of these reagents.

In many oil fields large volumes of water are produced and must be disposed of where water flooding operations are not in use or where water flooding operations cannot handle the amount of produced water. Most States have laws restricting pollution of streams and land with produced waters, and oil producers must then find some method of disposing of the waste produced salt water. In many instances therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compounds of this invention can also be used in such water disposal wells thus providing a simple and economical method of solving the corrosion problems encountered in disposing of unwanted water.

Water flood and waste disposal operations are too well known to require further elaboration. In essence, the flooding operation is effected in the conventional manner except that the flooding medium contains a minor amount of these compounds, sufficient to prevent corrosion.

While the flooding medium employed in accordance with the present invention contains water or oil field brine and the compounds of this invention, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc. and in conjunction with other secondary recovery methods.

The concentration of the corrosion inhibitors of this invention will vary widely depending on the particular compound, the particular system, etc. Concentrations of at least about ¼ ppm, such as about ¾ to 7,500 ppm for example about 1 to 5,000 ppm, advantageously about 10 to 1,000 ppm, but preferably about 15–250 ppm may be employed. Larger amounts can also be employed such as 1.5–5.0% although there is generally no commercial advantage in so doing.

For example, since the success of a water flooding operation manifestly depends upon its total cost being less than the value of the additional oil recovered from the oil reservoir, it is quite important to use as little as possible of these compounds consistent with optimum corrosion inhibition. Since these compounds are themselves inexpensive and are used in low concentrations, they enhance the success of a flood operation by lowering the cost thereof.

By varying the constituents of the composition, the compounds of this invention can be made more oil or more water soluble, depending on whether the composition is to be employed in oil or water systems.

Although the manner of practicing the present invention is clear from the foregoing description, the following non-limiting specific examples are included for purposes of illustration.

CORROSION TESTS

The test procedure includes measurement of the corrosive action of the fluids inhibited by the compositions herein described upon sand-blasted SAE-1020 steel coupons under conditions approximating those found in an actual producing well, and the comparison thereof with results obtained by subjecting identical test coupons to the corrosive action of the identical fluids containing no inhibitor.

In the present tests clean pint bottles are charged with 440 ml of a synthetic brine, which contains 42g of sodium chloride, 14g calcium chloride, 1g of sodium sulfate and 17g of magnesium chloride per liter, saturated with hydrogen-sulfide or air and a predetermined amount of inhibitor is then added. The inhibitor concentration is based on the total volume of fluid. Bottle caps holding three coupons are then placed tightly on the bottles. The bottles are then placed on a wheel contained in an oven and rotated for 4 hours at 90°–95°F. Corrosion rates are then measured using the three coupons in each bottle as electrodes in conjunction with an instrument for measurement of instantaneous corrosion rates of the type shown in Ser. No. 332,399 filed Dec. 23, 1963. Percent protection is calculated from $$\frac{R_1 - R_2}{R_1} \times 100\%.$$

where $R_1$ is corrosion rate of uninhibited fluids $R_2$ is corrosion rate of inhibited fluids When the inhibitor was oil-soluble as contrasted to water-soluble, a two-phase system was used instead of the "all-brine system" and this simply consisted of using hydrogen sulfide saturated mineral spirits to replace 25% by volume of the brine.

The following examples are presented to illustrate the use of cyclic phosphonates described herein and are presented for purposes of illustration and not of limitation.

TABLE B

CORROSION INHIBITOR TESTS

| Composition | In $H_2S$ Saturated Brine Protection (ppm) | |
|---|---|---|
| Example 1 | 78% (50) | 78% (100) |
| Example 3 | 85% (50) | 88% (100) |
| Example 10 | 63% (100) | 67% (200) |

| Composition | In a Saturated Brine containing $O_2$ Protection (ppm) |
|---|---|
| Example 3 | 78% (200) |
| Example 10 | 78% (100) |

It is well known that most corrosion inhibitors of the film-forming or non-reducing type are not too effective in preventing corrosion in aerobic systems, i.e. containing air and/or oxygen. However, the compounds of this invention are particularly suitable for preventing corrosion in aerobic systems. For example, they are particularly suitable for systems containing oxygen such as found in "open" secondary recovery systems, cooling towers, and the like.

The composition of this invention can also be employed in conjunction with other corrosion inhibitors, for example of the film-forming type. Non-limiting examples include the acylated polyamines such as described in U.S. Pat. Nos. Re.23,227, 2,466,517, 2,468,163, 2,598,213 and 2,640,029. These acylated polyamines may be described as amides, imidazolines, tetrahydropyrimidines, etc.

WATER CLARIFICATION

This phase of the present invention relates to a method for the clarification of water containing suspended matter.

Accordingly clarification of water containing suspended particles of matter is effected by adding to such water compounds of this invention.

Water containing suspended particles which may be treated by the present invention may have its origin either in natural or artificial sources, including industrial and sanitary sources. Waters containing suspended particles of natural origin are usually surface waters, wherein the particles are suspended soil particles (silt), although sub-surface waters may also be treated according to the present invention. Water having its origin in industrial process (including sanitary water) operations may contain many different varieties of suspended particles. These particles are generally the result of the particular industrial or sanitary operation concerned. Prior to discharging such industrial waste waters into natural water course it generally is desired that the suspended matter be removed.

The present process may likewise be applied to water contained in stock or fish ponds, lakes or other natural or artificial bodies of water containing suspended solids. It may be applied to industrial water supplied either in preparation therefor, during or after use and prior to disposal. It may be applied to sanitary water supplies either for the elimination of suspended solids prior to use for such purposes, or it may be applied to such waters which have become contaminated with impurities from any source.

Most naturally occurring waters contain an amount of simple electrolytes (sodium, potassium, ammonium, calcium, aluminum salts, etc.) in excess of that necessary for the initial aggregation of the ultimate silt particles. This is likewise true of particles of suspended material in industrial or sanitary waters. The ultimate particles of silt or other materials are therefore naturally somewhat aggregated by reason of the presence of such electrolytes. However, the forces binding such ultimate particles together are not great and moreover are not such as to generally effect either rapid settling rates of the flocculated material or strong enough to prevent deflocculation.

The compounds of this invention cause rapid flocculation and also reinforce the formed aggregates of particles causing a general tightening or bonding together of the initial particles and an increased rate of coagulation and settling, thus forming a less turbid supernatant liquid.

The addition of the compounds of this invention to the water suspension should be made in such a fashion that the resulting flocculation and aggregation of the particles takes place uniformly throughout the body of water. In order to obtain a uniform addition of the compositions of the invention to the water-borne suspension it is generally desirable to prepare a relatively dilute stock solution of the compositions and then to add such solution to the body of water in the proportions indicated. Clarification may take place either in the natural body of water or it may be caused to take place in hydraulic thickeners of known design.

The amount of the compositions to be employed will vary depending upon the amount and the degree of subdivision of the solids to be agglomerated or flocculated, the chemical nature of such solid and the particular inventive compositions employed. In general, I employ at least a sufficient amount of the compositions to promote flocculation. In general, I employ 0.005–10,000 ppm or more such as about 0.5–1,000 ppm, for example about 1–500 ppm, but preferably about 2–5ppm. Since the economics of these processes are important, no more than the minimum amount required for efficient removal is generally employed. It is desired, of course, to employ sufficient compositions so flocculation will take place without causing the formation of stable dispersions.

The precipitating action of the compositions can be employed in the application of loading or filling materials to textiles or paper.

In the processing of fine mineral particles in aqueous suspension the flocculating agents will be especially useful. In the processing of ores to separate valuable mineral constituents from undesirable matrix constituents, it is frequent practice to grind the ore into a finely-divided state to facilitate separation steps such as selective flotation and the like. In many ore dressing procedures, the finely-divided ore is suspended in water to form a pulp or slime. After processing, it is usually desirable to dewater the pulps or slimes either by sedimentation or filtering. In such operations, certain ores are particularly troublesome in that the finely-divided ore, when suspended in water, forms a stable slime which settles very slowly, if at all. Such slimes are unsuitable for concentration or dewatering by sedimentation and are difficult to dewater by filtration because of the tendency to clog the pores of the filter, thus leading to excessively time-consuming and inefficient operation of the filters. In some cases, for example, in certain phosphate mining operations, the formation of very stable suspensions of finely-divided mineral results not only in the loss of considerable valuable mineral as waste but also requires large expenditures for the maintenance of holding ponds for the waste. Similar problems are involved in processing gold, copper, nickel, lead, zinc, iron, such as taconite ores, uranium and other ores, and the inventive flocculating agents will be useful in these operations.

Some specific additional applications for the compositions of this invention, not intended to be limiting but merely illustrative are listed below. The compositions can be used for the clarification of beers or wines during manufacture. Another use is in processng effluents in pharmaceutical operations for the recovery of valuable products or removal of undesirable by-products. A particularly important use for these flocculating agents is in the clarification of both beet sugar and cane sugar juices in their processing. Still another use is for flocculation and recovery of pigments from aqueous suspensions thereof. The compositions will be particularly useful in sewage treatment operations as a flocculating agent. A further use is to promote by flocculation the removal of coal from aqueous suspensions thereof. In other words, the flocculating agents of the invention are generally useful for processing aqueous effluents of all types to facilitate the removal of suspended solids.

A water soluble or water dispersible compound, to the extent of effective concentration, is employed.

These compositions can also be employed in the process of flocculating white water and/or recycling of the precipitate solids in the paper making process described in U.S. Patent Application Ser. No. 347,023, filed Feb. 24, 1964, and other processes described therein.

Although the manner of practicing the present invention is clear from the foregoing description, the following non-limiting specific examples are included for purposes of illustration.

Naturally occurring water from many sources, and in some instances, brine and brackish waters are used in the recovery of petroleum by secondary water-flooding operations. Clarification of the water is necessary in many instances prior to water flooding because the suspended impurities tend to plug the underground formations into which waters are pumped.

EXAMPLES

A suspension of FeS in brine was subjected to the action of the water-soluble compounds prepared herein.

In these tests, the FeS concentration is 25 parts per million and 1% and 5% brine solution were used. Metered quantities (500 ml.) of the homogeneous suspension were placed into 1000 ml. beakers and stirred at 100 rpm. The compound to be tested was injected into the suspension to give final active concentrations varying between 2 through 4 parts per million. Stirring was achieved by use of a Phipp and Bird "floc" multi-stirrer. After one minute the stirring rate was reduced to 20 to 30 rmp and maintained thus for 10 minutes. At this time the stirring was stopped. The evaluation of the compound started at the moment of flocculation and continued with respect to the "floc" size and rate of precipitation. The final evaluation was achieved by visual examination of the color of the resultant aqueous phase.

The compositions described herein such as those prepared in the specific Examples are employed as flocculating agent.

These compounds are also effective in flocculating the other systems described herein.

The following is a partial list of industrial systems in which the compounds of the present invention can be employed as flocculating agents.

1. Petroleum industry
2. Food industry such as in the dairy industry, the canning, freezing and dehydration industries
3. Metal plating industry
4. Chemical and pharmaceutical industries
5. Mining industry, for example, in the phosphate mining industry such as in phosphate slimes
6. Fermentation industries, such as in alcohol, beer, yeast, antibiotics, etc. production
7. Tanning industry
8. Meat packing and slaughter house industry
9. Textile industry
10. Sugar refining industry
11. Coal industry
12. Soap industry
13. Sewage purification
14. Corn starch industry
15. Fat processing and soap industry
16. Paper industry
17. Hydroelectric plants, atomic energy operations, boiler plants, etc.

EXAMPLES

The commpositions described herein, such as those prepared in the specific Examples, are effective flocculants.

OTHER DERIVATIVES

These products may be further reacted to form derivatives thereof, for example, they may be oxyalkylated with alkylene oxides such as ethylene oxide, propylene oxide, butylene oxide, octylene oxide, alone or in combination; with styrene oxide, glycide, methyl glycide, allyl glycidyl ether, glycidyl isopropyl ether, glycidyl phenylether, diepoxides, polyepoxides, etc.

They may be reacted with alkylene imines such as ethyleneimine, propylene imine, etc., dialkylamino-epoxypropane of the structure

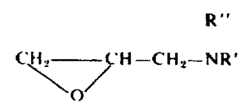

where the R's are alkyl, etc.

OTHER USES

In addition to the uses described above, these compositions and/or derivatives thereof, can be used as follows:

1. as demulsifiers for water-in-oil and oil-in-water emulsions
2. as biocides i.e. bacteriocides, algicides, etc.
3. as additives to various petroleum fuels including gasoline, diesel fuel, jet fuels, etc.
4. as gasoline anti-icers and anti-stallers
5. as flotation agents, such as flotation collection agents
6. as emulsifiers, for example, in metal cleaners, auto polishes, wax emulsions, etc.
7. as additives for sludging oil and cutting oils
8. as fuel "dehazing" agents
9. as agents for preparing emulsions for the "hydrofrac" process of enhancing oil recovery
10. as agents to prepare polymer emulsions
11. as agents for the textile industry such as mercerizing assistants, wetting agents, rewetting agents, penetrating agents, dispersing agents, softening agents, dyeing assistants, etc.
12. as anti-static agents for textiles, plastics, etc.
13. as agents in leather processing
14. as lube oil additives
15. as emulsifiers for insecticidal and agricultural compositions
16. as additives for primer paints to help insure adhesion to metallic surfaces and give corrosion protection
17. as additives useful as a freeze-thaw stabilizer for latex-base paints
18. as agents for the pulp and paper industry, such as sizing aids, etc.
19. as general metal deactivators

Having thus described my invention, what I claim as new and desire to obtain by Letters Patent is:

1. The piperazine phosphonic acids and derivatives thereof selected from the group consisting of (1) 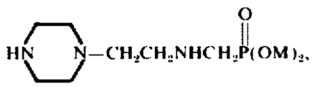

2. a mixture of

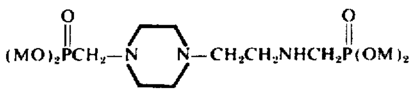 and

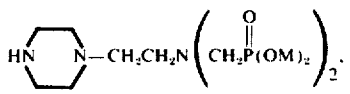

(3) 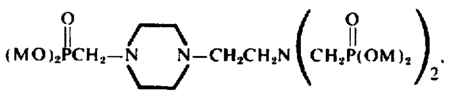

and 4. a mixture of

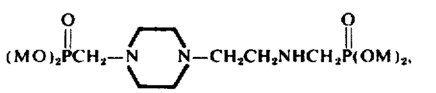

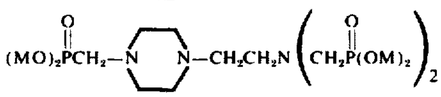 and

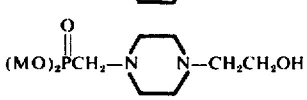

where M is hydrogen, alkali metal, ammonium, triethanolamine or diethanolamine.

2. The piperazine phosphonic acids of claim 1 where M is hydrogen.

3. The piperazine phosphonic acids of claim 2 which are a mixture of

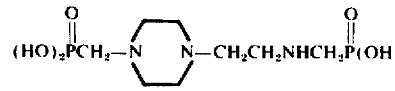

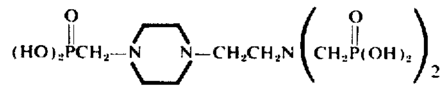 and

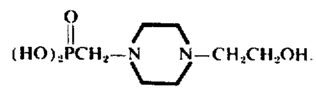

4. The piperazine phosphonic acids of claim 2 which are a mixture of

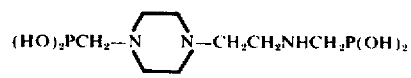

and

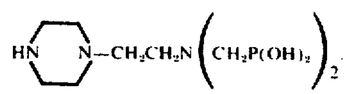

5. A piperazine phosphonic acid of claim 2 where said nitrogen phosphonic acid is

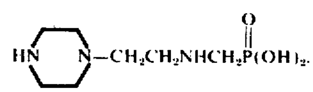

6. A piperazine phosphonic acid of claim 1 where said nitrogen heterocyclic phosphonic acid is

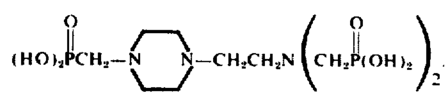

* * * * *